Figure 1:
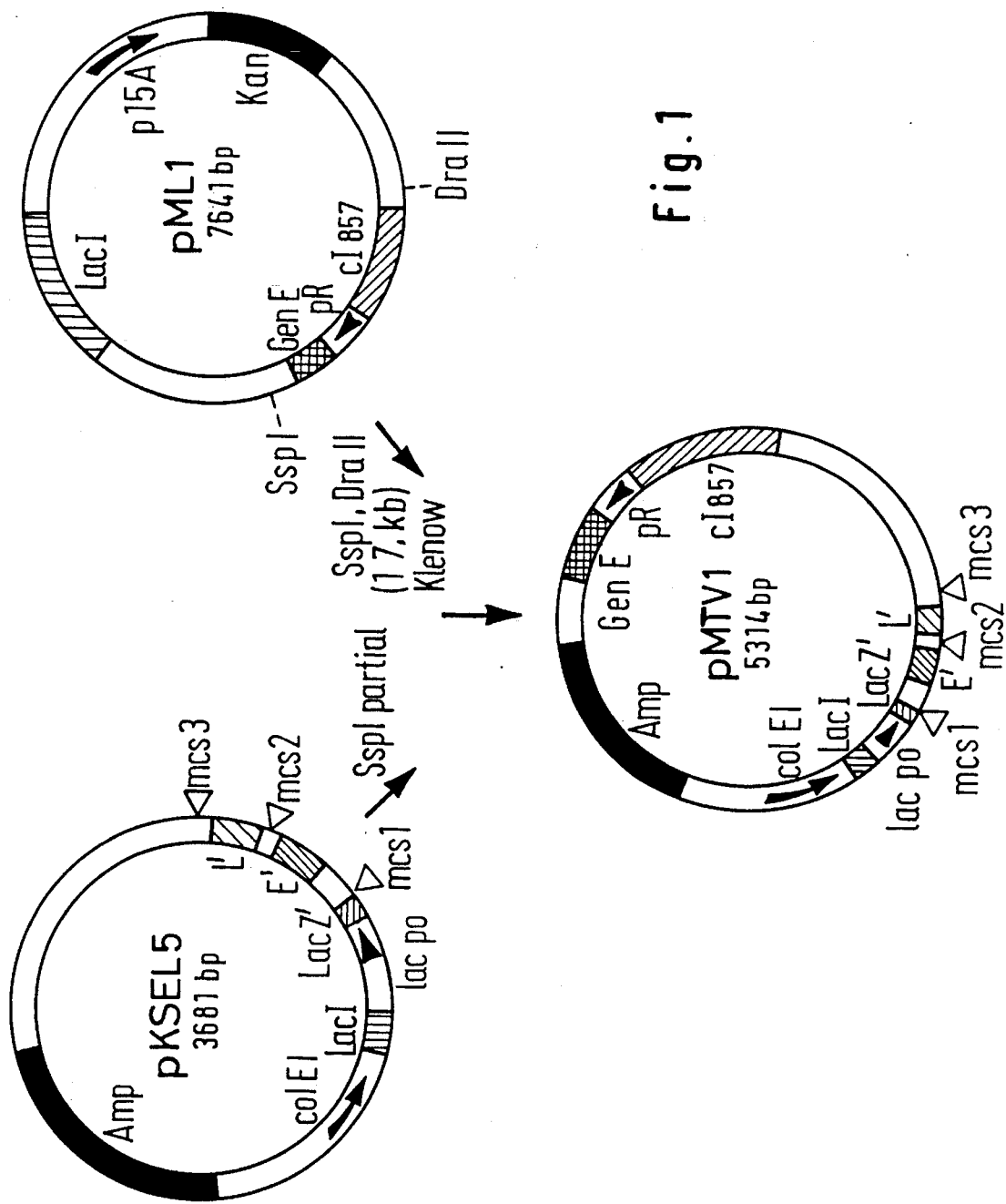
Figure 2A:
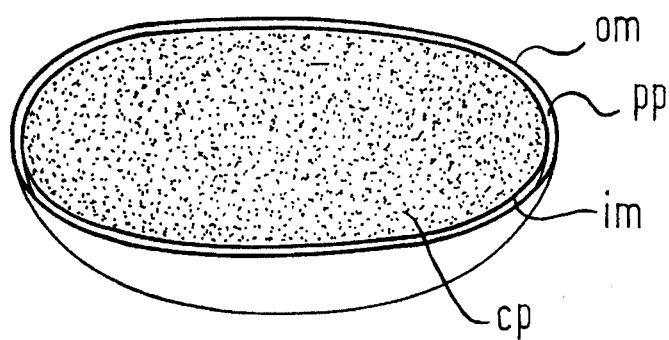
Figure 2B:
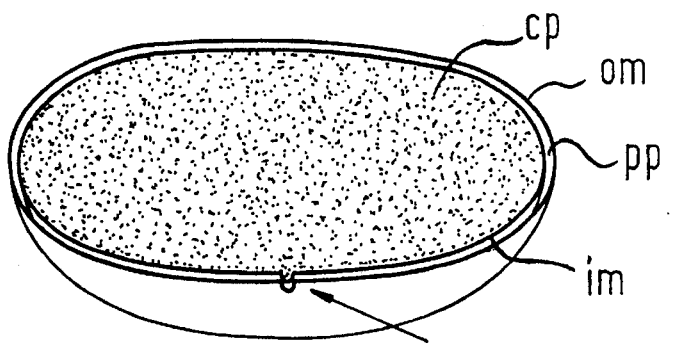
Figure 2C:
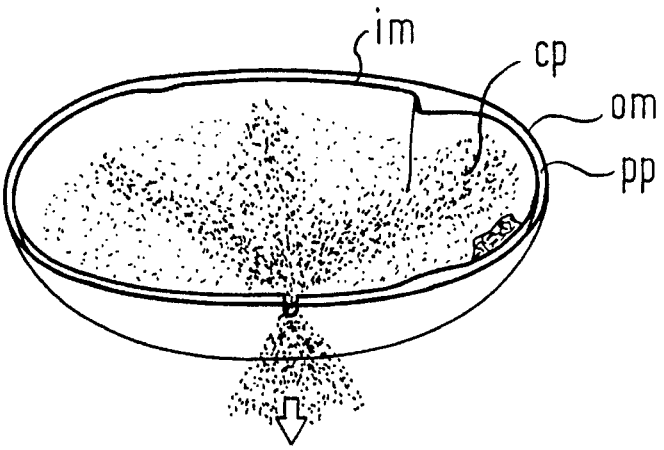
Figure 2D:
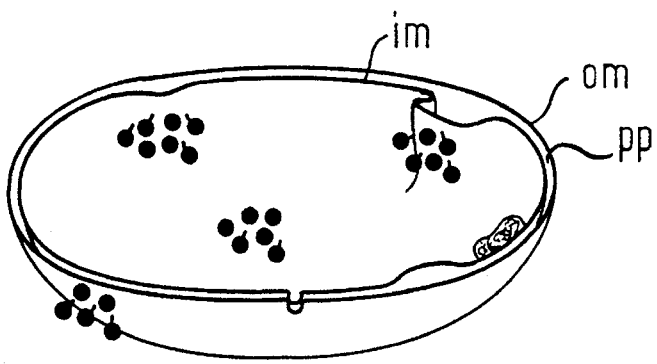

United States Patent [19]

Lubitz et al.

[11] Patent Number: 5,470,573
[45] Date of Patent: Nov. 28, 1995

[54] IMMUNOGENS COMPRISING THE NON-LYTIC MEMBRANE SPANNING DOMAIN OF BACTERIOPHAGES MS2 OR PHIX174

[75] Inventors: Werner Lubitz; Michael P. Szostak, both of Munich, Germany

[73] Assignee: Boehringer Mannheim GmbH, Mannheim, Germany

[21] Appl. No.: 924,028

[22] PCT Filed: Feb. 19, 1991

[86] PCT No.: PCT/EP91/00308

§ 371 Date: Sep. 30, 1992

§ 102(e) Date: Sep. 30, 1992

[87] PCT Pub. No.: WO91/13155

PCT Pub. Date: Sep. 5, 1991

[51] Int. Cl.$^6$ .................. A61K 39/02; A61K 39/108; C07K 14/195; C07K 14; C07K 245
[52] U.S. Cl. .................. 424/200.1; 424/184.1; 424/185.1; 424/234.1; 424/192.1; 424/194.1; 424/197.1; 424/200.1; 424/203.1; 424/241.1; 424/282.1; 435/69.3; 435/172.3; 530/350; 530/825; 530/403; 530/812; 536/23.4; 536/23.7; 514/2
[58] Field of Search .................. 424/88, 89, 184.1, 424/185.1, 234.1, 192.1–194.1, 197.11, 200.1, 203.1, 241.1, 282.1; 435/69.3, 69.7, 172.3; 530/403, 350, 825, 812; 536/23.4, 23.7; 514/2

[56] References Cited

U.S. PATENT DOCUMENTS 4,839,293  6/1989  Cantor et al. .................. 435/320

5,075,223  12/1991  Lubitz et al. .................. 435/69.1

FOREIGN PATENT DOCUMENTS

WO87/06590  of 0000  WIPO .

OTHER PUBLICATIONS

Maratea, D et al. Gene 40: 39–46 (1985).

Harkness, R. E. et al. FEMS Microbiol. Lett. 48: 19–24 (1987).

Szostak, M. et al. Res. Microbiol. 141: 1005–1007.

*Primary Examiner*—Christine M. Nucker
*Assistant Examiner*—Michael Tuscan
*Attorney, Agent, or Firm*—Felfe & Lynch

[57] ABSTRACT

The invention concerns a carrier-bound recombinant protein obtainable by expression of a fusion protein gene in gram-negative bacteria which codes for at least one hydrophobic non-lytically active protein domain capable of membrane integration as well as the recombinant protein and of a gene which codes for a lytically active membrane protein from bacteriophages or a lytically active toxin release gene or lytically active partial sequences thereof and isolation of the carrier-bound recombinant protein from the culture broth. The recombinant protein is thereby firmly incorporated into the cell wall complex of gram-negative bacteria via a target sequence. Furthermore the invention concerns a recombinant DNA for the production of the protein, the production process as well as the use of carrier-bound recombinant proteins according to the present invention for immunization and as vaccines.

8 Claims, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 1451 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GTCGACCTGC  AGGCATGCAA  GCTGATCTTC  AGACCTGGAG  GAGGAGATAT  GAGGGACAAT       60

TGGAGAAGTG  AATTATATAA  ATATAAAGTA  GTAAAAATTG  AACCATTAGG  AGTAGCACCC      120

ACCAAGGCAA  AGAGAAGAGT  GGTGCAGAGA  GAAAAAAGAG  CAGTGGGAAT  AGGAGCTTTG      180

TTCCTTGGGT  TCTTGGGAGC  AGCAGGAAGC  ACTATGGGCG  CAGCGTCAAT  GACGCTGACG      240

GTACAGGCCA  GACAATTATT  GTCTGGTATA  GTGCAGCAGC  AGAACAATTT  GCTGAGGGCT      300

ATTGAGGGCC  AACAGCATCT  GTTGCAACTC  ACAGTCTGGG  GCATCAAGCA  GCTCCAGGCA      360

AGAATCCTGG  CTGTGGAAAG  ATACCTAAAG  GATCAACAGC  TCCTGGGGAT  TTGGGGTTGC      420

TCTGGAAAAC  TCATTTGCAC  CACTGCTGTG  CCTTGGAATG  CTAGTTGGAG  TAATAAATCT      480

CTGGAACAGA  TTTGGAATAA  CATGACCTGG  ATGGAGTGGG  ACAGAGAAAT  TAACAATTAC      540

ACAAGCTTAA  TACACTCCTT  AATTGAAGAA  TCGCAAAACC  AGCAAGAAAA  GAATGAACAA      600
```

```
GAATTATTGG  AATTAGATAA  ATGGGCAAGT  TTGTGGAATT  GGTTTAACAT  AACAAATTGG   660
CTGTGGTATA  TAAAATTATT  CATAATGATA  GTAGGAGGCT  TGGTAGGTTT  AAGAATAGTT   720
TTTGCTGTAC  TTTCTATAGT  GAATAGAGTT  AGGCAGGGAT  ATTCACCATT  ATCGTTTCAG   780
ACCCACCTCC  CAAACCCGAG  GGACCCGAC   AGGCCCGAAG  GAATAGAAGA  AGAAGGTGGA   840
GAGAGAGACA  GAGACAGATC  CATTCGATTA  GTGAACGGAT  CCTTAGCACT  TATCTGGGAC   900
GATCTGCGGA  GCCTGTGCCT  CTTCAGCTAC  CACCGCTTGA  GAGACTTACT  CTTGATTGTA   960
ACGAGGATTG  TGGAACTTCT  GGGACGCAGG  GGGTGGGAAG  CCCTCAAATA  TTGGTGGAAT  1020
CTCCTACAGT  ATTGGAGTCA  GGAACTAAAG  AATAGTGCTG  TTAACTTGCT  CAATGCCACA  1080
GCTATAGCAG  TAGCTGAGGG  GACAGATAGG  GTTATAGAAT  TAGTACAAGC  AGCTTATAGA  1140
GCCATTCGCC  ACATACCTAG  AAGAATAAGA  CAGGGCTTGG  AAAGGATTTT  GCTATAAGAT  1200
GGGTGGCAAG  TGGTCAAAAA  GTAGTGTGGT  TGGATGGCCT  GCTGTAAGGG  AAAGAATGAG  1260
ACGAGCTGAG  CCAGCAGCAG  ATGGGGTGGG  AGCAGTATCT  CGAGACCTAG  AAAAACATGG  1320
AGCAATCACA  AGTAGCAATA  CAGCAGCTAC  CAATGCCGAT  TGTGCTTGGC  TAGAAGCACA  1380
AGAGGAGGAG  GAGGTGGGTT  TTCCAGTCAC  ACCTCAGGTA  CCTTTAAGAC  CAATGACTTA  1440
CAAGGCAGCT  G                                                           1451
```

( 2 ) INFORMATION FOR SEQ ID NO: 2:

( i ) SEQUENCE CHARACTERISTICS:
        ( A ) LENGTH: 525 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
TCTAGAACTA  GTGGATCCAT  CGAGGGTAGG  TCTATGGACC  CGTCCAAGGA  CTCCAAAGCT   60
CAGGTTTCTG  CAGCCGAAGC  TGGTATCACT  GGCACCTGGT  ATAACCAACT  GGGGTCGACT  120
TTCATTGTGA  CCGCTGGTGC  GGACGGAGCT  CTGACTGGCA  CCTACGAATC  TGCGGTTGGT  180
AACGCAGAAT  CCCGCTACGT  ACTGACTGGC  CGTTATGACT  CTGCACCTGC  CACCGATGGC  240
TCTGGTACCG  CTCTGGGCTG  GACTGTGGCT  TGGAAAAACA  ACTATCGTAA  TGCGCACAGC  300
GCCACTACGT  GGTCTGGCCA  ATACGTTGGC  GGTGCTGAGG  CTCGTATCAA  CACTCAGTGG  360
CTGTTAACAT  CCGGCACTAC  CGAAGCGAAT  GCATGGAAAT  CGACACTAGT  AGGTCATGAC  420
ACCTTTACCA  AAGTTAAGCC  TTCTGCTGCT  AGCATTGATG  CTGCCAAGAA  AGCAGGCGTA  480
AACAACGGTA  ACCCTCTAGA  CGCTGTTCAG  CAATAATAAG  GATCC                   525
```

( 2 ) INFORMATION FOR SEQ ID NO: 3:

( i ) SEQUENCE CHARACTERISTICS:
        ( A ) LENGTH: 3152 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
ATGACCATGA  TTACGAATTG  CTGCAGGTCG  ACGGATCCCG  TCGTTTTACA  ACGTCGTGAC   60
TGGGAAAACC  CTGGCGTTAC  CCAACTTAAT  CGCCTTGCAG  CACATCCCCC  TTTCGCCAGC  120
TGGCGTAATA  GCGAAGAGGC  CCGCACCGAT  CGCCCTTCCC  AACAGTTGCG  CAGCCTGAAT  180
GGCGAATGGC  GCTTTGCCTG  GTTTCCGGCA  CCAGAAGCGG  TGCCGGAAAG  CTGGCTGGAG  240
```

```
TGCGATCTTC CTGAGGCCGA TACTGTCGTC GTCCCCTCAA ACTGGCAGAT GCACGGTTAC    300
GATGCGCCCA TCTACACCAA CGTAACCTAT CCCATTACGG TCAATCCGCC GTTTGTTCCC    360
ACGGAGAATC CGACGGGTTG TTACTCGCTC ACATTTAATG TTGATGAAAG CTGGCTACAG    420
GAAGGCCAGA CGCGAATTAT TTTTGATGGC GTTAACTCGG CGTTTCATCT GTGGTGCAAC    480
GGGCGCTGGG TCGGTTACGG CCAGGACAGT CGTTTGCCGT CTGAATTTGA CCTGAGCGCA    540
TTTTTACGCG CCGGAGAAAA CCGCCTCGCG GTGATGGTGC TGCGTTGGAG TGACGGCAGT    600
TATCTGGAAG ATCAGGATAT GTGGCGGATG AGCGGCATTT CCGTGACGT CTCGTTGCTG    660
CATAAACCGA CTACACAAAT CAGCGATTTC CATGTTGCCA CTCGCTTTAA TGATGATTTC    720
AGCCGCGCTG TACTGGAGGC TGAAGTTCAG ATGTGCGGCG AGTTGCGTGA CTACCTACGG    780
GTAACAGTTT CTTTATGGCA GGGTGAAACG CAGGTCGCCA GCGGCACCGC GCCTTTCGGC    840
GGTGAAATTA TCGATGAGCG TGGTGGTTAT GCCGATCGCG TCACACTACG TCTGAACGTC    900
GAAAACCCGA AACTGTGGAG CGCCGAAATC CCGAATCTCT ATCGTGCGGT GGTTGAACTG    960
CACACCGCCG ACGGCACGCT GATTGAAGCA GAAGCCTGCG ATGTCGGTTT CCGCGAGGTG   1020
CGGATTGAAA ATGGTCTGCT GCTGCTGAAC GGCAAGCCGT TGCTGATTCG AGGCGTTAAC   1080
CGTCACGAGC ATCATCCTCT GCATGGTCAG GTCATGGATG AGCAGACGAT GGTGCAGGAT   1140
ATCCTGCTGA TGAAGCAGAA CAACTTTAAC GCCGTGCGCT GTTCGCATTA TCCGAACCAT   1200
CCGCTGTGGT ACACGCTGTG CGACCGCTAC GGCCTGTATG TGGTGGATGA AGCCAATATT   1260
GAAACCCACG GCATGGTGCC AATGAATCGT CTGACCGATG ATCCGCGCTG GCTACCGGCG   1320
ATGAGCGAAC GCGTAACGCG AATGGTGCAG CGCGATCGTA ATCACCCGAG TGTGATCATC   1380
TGGTCGCTGG GGAATGAATC AGGCCACGGC GCTAATCACG ACGCGCTGTA TCGCTGGATC   1440
AAATCTGTCG ATCCTTCCCG CCCGGTGCAG TATGAAGGCG GCGGAGCCGA CACCACGGCC   1500
ACCGATATTA TTTGCCCGAT GTACGCGCGC GTGGATGAAG ACCAGCCCTT CCCGGCTGTG   1560
CCGAAATGGT CCATCAAAAA ATGGCTTTCG CTACCTGGAG AGACGCGCCC GCTGATCCTT   1620
TGCGAATACG CCCACGCGAT GGGTAACAGT CTTGGCGGTT TCGCTAAATA CTGGCAGGCG   1680
TTTCGTCAGT ATCCCCGTTT ACAGGGCGGC TTCGTCTGGG ACTGGGTGGA TCAGTCGCTG   1740
ATTAAATATG ATGAAAACGG CAACCCGTGG TCGGCTTACG GCGGTGATTT TGGCGATACG   1800
CCGAACGATC GCCAGTTCTG TATGAACGGT CTGGTCTTTG CCGACCGCAC GCCGCATCCA   1860
GCGCTGACGG AAGCAAAACA CCAGCAGCAG TTTTTCCAGT TCCGTTTATC CGGGCAAACC   1920
ATCGAAGTGA CCAGCGAATA CCTGTTCCGT CATAGCGATA ACGAGCTCCT GCACTGGATG   1980
GTGGCGCTGG ATGGTAAGCC GCTGGCAAGC GGTGAAGTGC CTCTGGATGT CGCTCCACAA   2040
GGTAAACAGT TGATTGAACT GCCTGAACTA CCGCAGCCGG AGAGCGCCGG CAACTCTGG   2100
CTCACAGTAC GCGTAGTGCA ACCGAACGCG ACCGCATGGT CAGAAGCCGG GCACATCAGC   2160
GCCTGGCAGC AGTGGCGTCT GGCGGAAAAC CTCAGTGTGA CGCTCCCCGC CGCGTCCCAC   2220
GCCATCCCGC ATCTGACCAC CAGCGAAATG GATTTTTGCA TCGAGCTGGG TAATAAGCGT   2280
TGGCAATTTA ACCGCCAGTC AGGCTTTCTT TCACAGATGT GGATTGGCGA TAAAAAACAA   2340
CTGCTGACGC CGCTGCGCGA TCAGTTCACC CGTGCACCGC TGGATAACGA CATTGGCGTA   2400
AGTGAAGCGA CCCGCATTGA CCCTAACGCC TGGGTCGAAC GCTGGAAGGC GGCGGGCCAT   2460
TACCAGGCCG AAGCAGCGTT GTTGCAGTGC ACGGCAGATA CACTTGCTGA TGCGGTGCTG   2520
ATTACGACCG CTCACGCGTG GCAGCATCAG GGGAAAACCT TATTTATCAG CCGGAAAACC   2580
TACCGGATTG ATGGTAGTGG TCAAATGGCG ATTACCGTTG ATGTTGAAGT GGCGAGCGAT   2640
```

```
ACACCGCATC  CGGCGCGGAT  TGGCCTGAAC  TGCCAGCTGG  CGCAGGTAGC  AGAGCGGGTA   2700
AACTGGCTCG  GATTAGGGCC  GCAAGAAAAC  TATCCCGACC  GCCTTACTGC  CGCCTGTTTT   2760
GACCGCTGGG  ATCTGCCATT  GTCAGACATG  TATACCCCGT  ACGTCTTCCC  GAGCGAAAAC   2820
GGTCTGCGCT  GCGGGACGCG  CGAATTGAAT  TATGGCCCAC  ACCAGTGGCG  CGGCGACTTC   2880
CAGTTCAACA  TCAGCCGCTA  CAGTCAACAG  CAACTGATGG  AAACCAGCCA  TCGCCATCTG   2940
CTGCACGCGG  AAGAAGGCAC  ATGGCTGAAT  ATCGACGGTT  CCATATGGG   GATTGGTGGC   3000
GACGACTCCT  GGAGCCCGTC  AGTATCGGCG  GAATTCCAGC  TGAGCGCCGG  TCGCTACCAT   3060
TACCAGTTGG  TCTGGTGTCA  AAAATAATAA  TAACCGGGCA  GGCCATGTCT  GCCCGTATTT   3120
CGCGTAAGGA  AATCCATTAT  GTACTATTTA  AA                                  3152
```

( 2 ) INFORMATION FOR SEQ ID NO: 4:

( i ) SEQUENCE CHARACTERISTICS:
        ( A ) LENGTH: 5314 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
AAATTGTAAA  CGTTAATATT  AGACATAATT  TATCCTCAAG  TAAGGGGCCG  AAGCCCCTGC     60
AATTAAAATT  GTTGACCACC  TACATACCAA  AGACGAGCGC  CTTTACGCTT  GCCTTTAGTA    120
CCTCGCAACG  GCTGCGGACG  ACCAGGGCGA  GCGCCAGAAC  GTTTTTACC   TTTAGACATT    180
ACATCACTCC  TTCCGCACGT  AATTTTTGAC  GCACGTTTTC  TTCTGCGTCA  GTAAGAACGT    240
CAGTGTTTCC  TGCGCGTACA  CGCAAGGTAA  ACGCGAACAA  TTCAGCGGCT  TTAACCGGAC    300
GCTCGACGCC  ATTAATAATG  TTTTCCGTAA  ATTCAGCGCC  TTCCATGATG  AGACAGGCCG    360
TTTGAATGTT  GACGGGATGA  ACATAATAAG  CAATGACGGC  AGCAATAAAC  TCAACAGGAG    420
CAGGAAAGCG  AGGGTATCCC  ACAAAGTCCA  GCGTACCATA  AACGCAAGCC  TCAACGCAGC    480
GACGAGCACG  AGAGCGGTCA  GTAGCAATCC  AAACTTTGTT  ACTCGTCAGA  AAATCGAAAT    540
CATCTTCGGT  TAAATCCAAA  ACGGCAGAAG  CCTGAATTCT  AGCTAGAGGA  TCTTTAGCTG    600
TCTTGGTTTG  CCCAAAGCGC  ATTGCATAAT  CTTTCAGGGT  TATGCGTTGT  TCCATACAAC    660
CTCCTTAGTA  CATGCAACCA  TTATCACCGC  CAGAGGTAAA  ATAGTCAACA  CGCACGGTGT    720
TAGATATTTA  TCCCTTGCGG  TGATAGATTT  AACGTATGAG  CACAAAAAAG  AAACCATTAA    780
CACAAGAGCA  GCTTGAGGAC  GCACGTCGCC  TTAAAGCAAT  TTATGAAAAA  AGAAAAATG    840
AACTTGGCTT  ATCCCAGGAA  TCTGTCGCAG  ACAAGATGGG  GATGGGGCAG  TCAGGCGTTG    900
GTGCTTTATT  TAATGGCATC  AATGCATTAA  ATGCTTATAA  CGCCGCATTG  CTTACAAAAA    960
TTCTCAAAGT  TAGCGTTGAA  GAATTTAGCC  CTTCAATCGC  CAGAGAAATC  TACGAGATGT   1020
ATGAAGCGGT  TAGTATGCAG  CCGTCACTTA  GAAGTGAGTA  TGAGTACCCT  GTTTTTTCTC   1080
ATGTTCAGGC  AGGGATGTTC  TCACCTAAGC  TTAGAACCTT  TACCAAAGGT  GATGCGGAGA   1140
GATGGGTAAG  CACAACCAAA  AAAGCCAGTG  ATTCTGCATT  CTGGCTTGAG  GTTGAAGGTA   1200
ATTCCATGAC  CGCACCAACA  GGCTCCAAGC  CAAGCTTTCC  TGACGGAATG  TTAATTCTCG   1260
TTGACCCTGA  GCAGGCTGTT  GAGCCAGGTG  ATTTCTGCAT  AGCCAGACTT  GGGGGTGATG   1320
AGTTTACCTT  CAAGAAACTG  ATCAGGGATA  GCGGTCAGGT  GTTTTACAA   CCACTAAACC   1380
CACAGTACCC  AATGATCCCA  TGCAATGAGA  GTTGTTCCGT  TGTGGGGAAA  GTTATCGCTA   1440
GTCAGTGGCC  TGAAGAGACG  TTTGGCTGAT  CGGCAAGGTG  TTCTGGTCGG  CGCATAGCTG   1500
```

```
ATAACAATTG AGCAAGAATC TTCATCGAAT TAGGGGAATT TTCACTCCCC TCAGAACATA    1560
ACATAGTAAA TGGATTGAAT TATGAAGAAT GGTTTTTATG CGACTTACCG CAGCAAAAAT    1620
AAAGGGAAAG ATACTTGAAG ACGAAAGGGC ATTTTGTTAA AATTCGCGTT AAATTTTTGT    1680
TAAATCAGCT CATTTTTTAA CCAATAGGCC GAAATCGGCA AAATCCCTTA TAAATCAAAA    1740
GAATAGACCG AGATAGGGTT GAGTGTTGTT CCAGTTTGGA ACAAGAGTCC ACTATTAAAG    1800
AACGTGGACT CCAACGTCAA AGGGCGAAAA ACCGTCTATC AGGGCGATGG CCCACTACGT    1860
GAACCATCAC CCTAATCAAG TTTTTTGGGG TCGAGGTGCC GTAAAGCACT AAATCGGAAC    1920
CCTAAAGGGA GCCCCCGATT TAGAGCTTGA CGGGGAAAGC CGGCGAACGT GGCGAGAAAG    1980
GAAGGGAAGA AAGCGAAAGG AGCGGGCGCT AGGGCGCTGG CAAGTGTAGC GGTCACGCTG    2040
CGCGTAACCA CCACACCCGC CGCGCTTAAT GCGCCGCTAC AGGGCGCGTC CCATTCGCCA    2100
TTCAGGCTAC GCAACTGTTG GGAAGGGCGA TCGGTGCGGG CCTCTTCGCT ATTACGCCAG    2160
CTGGCGAAGG GGGGATGTGC TGCAAGGCGA TTAAGTTGGG TAACGCCAGG GTTTTCCCAG    2220
TCACGACGTT GTAAAACGAC GGCCAGTGAA TTGTAATACG ACTCACTATA GGGCGAATTG    2280
GAGCTCCACC GCGGTGGCGG CCGCTCTAGT ATGGTGCACT CTCAGTACAA TCTGCTCTGA    2340
TGCCGCATAG TTAAGCCAGT ATATACACTC CGCTATCGCT ACGTGACTGG GTCATGGCTG    2400
CGCCCCGACA CCCGCCAACA CCCGCTGACG CGCCCTGACG GCTTGTCTG CTCCCGGCAT     2460
CCGCTTACAG ACAAGCTGTG ACCGTCTCCG GGAGCTGCAT GTGTCAGAGG TTTTCACCGT    2520
CATCACCGAA ACGCGCGAGG CAGTAAGGTC GGATGCTTTG TGAGCAATTC GTCCCTTAAG    2580
TAAGCAATTG CTGTAAAGTC GTCACTGTGC GGATCACCGC TTCCAGTAGC GACAGAAGCA    2640
ATTGATTGGT AAATTTCGAG AGAAAGATCG CGAGGAAGAT CAATACATAA AGAGTTGAAC    2700
TTCTTTGTTG TCTTCGACAT GGGTAATCCT CATGTTGAA TGGCCCTAGA GGATCCGGCC     2760
AAGCTTGCAT GCCTGCAGGT CGACTCTAGA GGATCCCCGA CGCTCGACGC CATTAATAAT    2820
GTTTTCCGTA AATTCAGCGC CTTCCATGAT GAGACAGGCC GTTTGAATGT TGACGGGATG    2880
AACATAATAA GCAATGACGG CAGCAATAAA CTCAACAGGA GCAGGAAAGC GAGGGTATCC    2940
CACAAAGTCC AGCGTACCAT AAACGCAAGC CTCAACGCAG CGACGAGCAC GAGAGCGGTC    3000
AGTAGCAATC CAAACTTTGT TACTCGTCAG AAAATCGAAA TCATCTTCGG TTAAATCCAA    3060
AACGGCAGAA GCCTGAATGA GAATTCGACC TCGAGGGGGG GCCCGGTACC CAGCTTTTGT    3120
TCCCTTTAGT GAGGGTTAAT TCCGAGCTTG GCGTAATCAT GGTCATAGCT GTTTCCTGTG    3180
TGAAATTGTT ATCCGCTCAC AATTCCACAC AACATAGGAG CCGGAAGCAT AAAGTGTAAA    3240
GCCTGGGGTG CCTAATGAGT GAGGTAACTC ACATTAATTG CGTTGCGCTC ACTGCCCGCT    3300
TTCCAGTCGG GAAACCTGTC GTGCCAGCTG CATTAATGAA TCGGCCAACG CGCGGGGAGA    3360
GGCGGTTTGC GTATTGGGCG CTCTTCCGCT TCCTCGCTCA CTGACTCGCT GCGCTCGGTC    3420
GTTCGGCTGC GGCGAGCGGT ATCAGCTCAC TCAAGGCGG TAATACGGTT ATCCACAGAA     3480
TCAGGGGATA ACGCAGGAAA GAACATGTGA GCAAAAGGCC AGCAAAAGGC CAGGAACCGT    3540
AAAAAGGCCG CGTTGCTGGC GTTTTTCCAT AGGCTCGGCC CCCCTGACGA GCATCACAAA    3600
AATCGACGCT CAAGTCAGAG GTGGCGAAAC CCGACAGGAC TATAAAGATA CCAGGCGTTC    3660
CCCCCTGGAA GCTCCCTCGT GCGCTCTCCT GTTCCGACCC TGCCGCTTAC CGGATACCTG    3720
TCCGCCTTTC TCCCTTCGGG AAGCGTGGCG CTTTCTCAAT GCTCACGCTG TAGGTATCTC    3780
AGTTCGGTGT AGGTCGTTCG CTCCAAGCTG GGCTGTGTGC ACGAACCCCC CGTTCAGCCC    3840
```

-continued

```
GACCGCTGCG CCTTATCCGG TAACTATCGT CTTGAGTCCA ACCCGGTAAG ACACGACTTA  3900
TCGCCACTGG CAGCAGCCAC TGGTAACAGG ATTAGCAGAG CGAGGTATGT AGGCGGTGCT  3960
ACAGAGTTCT TGAAGTGGTG GCCTAACTAC GGCTACACTA GAAGGACAGT ATTTGGTATC  4020
TGCGCTCTGC TGAAGCCAGT TACCTTCGGA AAAAGAGTTG GTAGCTCTTG ATCCGGCAAA  4080
CAAACCACCG CTGGTAGCGG TGGTTTTTTT GTTTGCAAGC AGCAGATTAC GCGCAGAAAA  4140
AAAGGATCTC AAGAAGATCC TTTGATCTTT TCTACGGGGT CTGACGCTCA GTGGAACGAA  4200
AACTCACGTT AAGGGATTTT GGTCATGAGA TTATCAAAAA GGATCTTCAC CTAGATCCTT  4260
TTAAATTAAA AATGAAGTTT TAAATCAATC TAAAGTATAT ATGAGTAAAC TTGGTCTGAC  4320
AGTTACCAAT GCTTAATCAG TGAGGCACCT ATCTCAGCGA TCTGTCTATT TCGTTCATCC  4380
ATAGTTGCCT GACTGCCCGT CGTGTAGATA ACTACGATAC GGGAGGGCTT ACCATCTGGC  4440
CCCAGTGCTG CAATGATACC GCGAGACCCA CGCTCACCGG CTCCAGATTT ATCAGCAATA  4500
AACCAGCCAG CCGGAAGGGC CGAGCGCAGA AGTGGTCCTG CAACTTTATC CGCCTCCATC  4560
CAGTCTATTA ATTGTTGCCG GGAAGCTAGA GTAAGTAGTT CGCCAGTTAA TAGTTTGCGC  4620
AACGTTGTTG CCATTGCTAC AGGCATCGTG GTGTCACGCT CGTCGTTTGG TATGGCTTCA  4680
TTCAGCTCCG GTTCCCAACG ATCAAGGCGA GTTACATGAT CCCCCATGTT GTGAAAAAAA  4740
GCGGTTAGCT CCTTCGGTCC TCCGATCGTT GTCAGAAGTA AGTTGGCCGC AGTGTTATCA  4800
CTCATGCTTA TGGCAGCACT GCATAATTCT CTTACTGTCA TGCCATCCGT AAGATGCTTT  4860
TCTGTGACTG GTGAGTACTC AACCAAGTCA TTCTGAGAAT AGTGTATGCG GCGACCGAGT  4920
TGCTCTTGCC CGGCGTCAAT ACGGGATAAT ACCGCGCCAC ATAGCAGAAC TTTAAAAGTG  4980
CTCATCATTG GAAAACGTTC TTCGGGGCGA AAACTCTCAA GGATCTTACC GCTGTTGAGA  5040
TCCAGTTCGA TGTAACCCAC TCGTGCACCC AACTGATCTT CAGCATCTTT TACTTTCACC  5100
AGCGTTTCTG GGTGAGCAAA AACAGGAAGG CAAAATGCCG CAAAAAGGG AATAAGGGCG  5160
ACACGGAAAT GTTGAATACT CATACTCTTC CTTTTTCAAT ATTATTGAAG CATTTATCAG  5220
GGTTATTGTC TCATGAGCGG ATACATATTT GAATGTATTT AGAAAAATAA ACAAATAGGG  5280
GTTCCGCGCA CATTTCCCCG AAAAGTGCCA CCTG                              5314
```

( 2 ) INFORMATION FOR SEQ ID NO: 5:

( i ) SEQUENCE CHARACTERISTICS:
        ( A ) LENGTH: 7641 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
GACGCCGGGC AAGAGCAACT CGGTCGCCGC ATACACTATT CTCAGAATGA CTTGGTTGAG   60
TACTCACCAG TCACAGAAAA GCATCTTACG GATGGCATGA CAGTAAGAGA ATTATGCAGT  120
GCTGCCATAA CCATGAGTGA TAACACTGCG GCCAACTTAC TTCTGACAAC GATCGGAGGA  180
CCGAAGGAGC TAACCGCTTT TTTGCACAAC ATGGGGGATC ATGTAACTCG CCTTGATCGT  240
TGGGAACCGG AGCTGAATGA AGCCATACCA AACGACGAGC GTGACACCAC GATGCCTGCA  300
GCAATGGCAA CAACGTTGCG CAAACTATTA ACTGGCGAAC TACTTACTCT AGCTTCCCGG  360
CAACAATTAA TAGACTGGAT GGAGGCGGAT AAAGTTGCAG GACCACTTCT GCGCTCGGCC  420
CTTCCGGCTG GCTGGTTTAT TGCTGATAAA TCTGGAGCCG GTGAGCGTGG GTCTCGCGGT  480
ATCATTGCAG CACTGGGGCC AGATGGTAAG CCCTCCCGTA TCGTAGTTAT CTACACGACG  540
```

```
GGGAGTCAGG  CAACTATGGA  TGAACGAAAT  AGACAGATCG  CTGAGATAGG  TGCCTCACTG   600
ATTAAGCATT  GGTAACTGTC  AGACCAAGTT  TACTCATATA  TACTTTAGAT  TGATTTAAAA   660
CTTCATTTTT  AATTTAAAAG  GATCTAGGTG  AAGATCCTTT  TTGATAATCT  CATGACCAAA   720
ATCCCTTAAC  GTGAGTTTTC  GTTCCACTGA  GCGTCAGACC  CCTTAATAAG  ATGATCTTCT   780
TGAGATCGTT  TTGGTCTGCG  CGTAATCTCT  TGCTCTGAAA  ACGAAAAAC   CGCCTTGCAG   840
GGCGGTTTTT  CGAAGGTTCT  CTGAGCTACC  AACTCTTTGA  ACCGAGGTAA  CTGGCTTGGA   900
GGAGCGCAGT  CACCAAAACT  TGTCCTTTCA  GTTAGCCTT   AACCGGCGCA  TGACTTCAAG   960
ACTAACTCCT  CTAAATCAAT  TACCAGTGGC  TGCTGCCAGT  GGTGCTTTTG  CATGTCTTTC  1020
CGGGTTGGAC  TCAAGACGAT  AGTTACCGGA  TAAGGCGCAG  CGGTCGGACT  GAACGGGGGG  1080
TTCGTGCATA  CAGTCCAGCT  TGGAGCGAAC  TGCCTACCCG  GAACTGAGTG  TCAGGCGTGG  1140
AATGAGACAA  ACGCGGCCAT  AACAGCGGAA  TGACACCGGT  AAACCGAAAG  GCAGGAACAG  1200
GAGAGCGCAC  GAGGGAGCCG  CCAGGGGAAA  CGCCTGGTAT  CTTTATAGTC  CTGTCGGGTT  1260
TCGCCACCAC  TGATTGAGC   GTCAGATTTC  GTGATGCTTG  TCAGGGGGC   GGAGCCTATG  1320
GAAAAACGGC  TTTGCCGCGG  CCCTCTCACT  TCCCTGTTAA  GTATCTTCCT  GGCATCTTCC  1380
AGGAAATCTC  CGCCCCGTTC  GTAAGCCATT  TCCGCTCGCC  GCAGTCGAAC  GACCGAGCGT  1440
AGCGAGTCAG  TGAGCGAGGA  AGCGGAATAT  ATCCTGTATC  ACATATTCTG  CTGACGCACC  1500
GGTGCAGCCT  TTTTTCTCCT  GCCACATGAA  GCACTTCACT  GACACCCTCA  TCAGTGCCAA  1560
CATAGTAAGC  CAGTATACAC  TCCGCTAGCG  CTGAGGTCTG  CCTCGTGAAG  AAGGTGTTGC  1620
TGACTCATAC  CAGGCCTGAA  TCGCCCCATC  ATCCAGCCAG  AAAGTGAGGG  AGCCACGGTT  1680
GATGAGAGCT  TTGTTGTAGG  TGGACCAGTT  GGTGATTTTG  AACTTTTGCT  TTGCCACGGA  1740
ACGGTCTGCG  TTGTCGGGAA  GATGCGTGAT  CTGATCCTTC  AACTCAGCAA  AGTTCGATT   1800
TATTCAACAA  AGCCACGTTG  TGTCTCAAAA  TCTCTGATGT  TACATTGCAC  AAGATAAAAA  1860
TATATCATCA  TGAACAATAA  AACTGTCTGC  TTACATAAAC  AGTAATACAA  GGGGTGTTAT  1920
GAGCCATATT  CAACGGGAAA  CGTCTTGCTC  GAGGCCGCGA  TTAAATTCCA  ACATGGATGC  1980
TGATTTATAT  GGGTATAAAT  GGGCTCGCGA  TAATGTCGGG  CAATCAGGTG  CGACAATCTA  2040
TCGATTGTAT  GGGAAGCCCG  ATGCGCCAGA  GTTGTTTCTG  AAACATGGCA  AAGGTAGCGT  2100
TGCCAATGAT  GTTACAGATG  AGATGGTCAG  ACTAAACTGG  CTGACGGAAT  TTATGCCTCT  2160
TCCGACCATC  AAGCATTTTA  TCCGTACTCC  TGATGATGCA  TGGTTACTCA  CCACTGCGAT  2220
CCCCGGGAAA  ACAGCATTCC  AGGTATTAGA  AGAATATCCT  GATTCAGGTG  AAAATATTGT  2280
TGATGCGCTG  GCAGTGTTCC  TGCGCCGGTT  GCATTCGATT  CCTGTTTGTA  ATTGTCCTTT  2340
TAACAGCGAT  CGCGTATTTC  GTCTCGCTCA  GGCGCAATCA  CGAATGAATA  ACGGTTTGGT  2400
TGATGCGAGT  GATTTTGATG  ACGAGCGTAA  TGGCTGGCCT  GTTGAACAAG  TCTGGAAAGA  2460
AATGCATAAG  CTTTTGCCAT  TCTCACCGGA  TTCAGTCGTC  ACTCATGGTG  ATTTCTCACT  2520
TGATAACCTT  ATTTTTGACG  AGGGGAAATT  AATAGGTTGT  ATTGATGTTG  GACGAGTCGG  2580
AATCGCAGAC  CGATACCAGG  ATCTTGCCAT  CCTATGGAAC  TGCCTCGGTG  AGTTTTCTCC  2640
TTCATTACAG  AAACGGCTTT  TTCAAAAATA  TGGTATTGAT  AATCCTGATA  TGAATAAATT  2700
GCAGTTTCAT  TTGATGCTCG  ATGAGTTTTT  CTAATCAGAA  TTGGTTAATT  GGTTGTAACA  2760
CTGGCAGAGC  ATTACGCTGA  CTTGACGGGA  CGGCGGCTTT  GTTGAATAAA  TCGAACTTTT  2820
GCTGAGTTGA  AGGATCAGAT  CACGCATCTT  CCCGACAACG  CAGACCGTTC  CGTGGCAAAG  2880
CAAAAGTTCA  AAATCACCAA  CTGGTCCACC  TACAACAAAG  CTCTCATCAA  CCGTGGCTCC  2940
```

-continued

```
CTCACTTTCT GGCTGGATGA TGGGGCGATT CAGGCCTGGT ATGAGTCAGC AACACCTTCT 3000
TCACGAGGCA GACCTCAGCG CTCAAAGATG CAGGGGTAAA AGCTAACCGC ATCTTTACCG 3060
ACAAGGCATC CGGCAGTTCA ACAGATCGGG AAGGGCTGGA TTTGCTGAGG ATGAAGGTGG 3120
AGGAAGGTGA TGTCATTCTG GTGAAGAAGC TCGACCGTCT TGGCCGCGAC ACCGCCGACA 3180
TGATCCAACT GATAAAGAG  TTTGATGCTC AGGGTGTAGC GGTTCGGTTT ATTGACGACG 3240
GGATCAGTAC CGACGGTGAT ATGGGGCAAA TGGTGGTCAC CATCCTGTCG GCTGTGGCAC 3300
AGGCTGAACG CCGGAGGATC CAGTTCGATG TAACCCACTC GTGCACCCAA CTGATCTTCA 3360
GCATCTTTTA CTTTCACCAG CGTTTCTGGG TGAGCAAAAA CAGGAAGGCA AATGCCGCA  3420
AAAAGGGAA  TAAGGGCGAC ACGGAAATGT TGAATACTCA TACTCTTCCT TTTTCAATAT 3480
TATTGAAGCA TTTATCAGGG TTATTGTCTC ATGAGCGGAT ACATATTTGA ATGTATTTAG 3540
AAAAATAAAC AAATAGGGGT TCCGCGCACA TTTCCCCGAA AAGTGCCACC TGACGTCTAA 3600
GAAACCATTA TTATCATGAC ATTAACCTAT AAAAATAGGC GTATCACGAG GCCCTTTCGT 3660
CTTCAAGTAT CTTTCCCTTT ATTTTGCTG  CGGTAAGTCG CATAAAAACC ATTCTTCATA 3720
ATTCAATCCA TTTACTATGT TATGTTCTGA GGGGAGTGAA AATTCCCCTA ATTCGATGAA 3780
GATTCTTGCT CAATTGTTAT CAGCTATGCG CCGACCAGAA CACCTTGCCG ATCAGCCAAA 3840
CGTCTCTTCA GGCCACTGAC TAGCGATAAC TTTCCCCACA ACGGAACAAC TCTCATTGCA 3900
TGGGATCATT GGGTACTGTG GGTTTAGTGG TTGTAAAAAC ACCTGACCGC TATCCCTGAT 3960
CAGTTTCTTG AAGGTAAACT CATCACCCCC AAGTCTGGCT ATGCAGAAAT CACCTGGCTC 4020
AACAGCCTGC TCAGGGTCAA CGAGAATTAA CATTCCGTCA GGAAAGCTTG GCTTGGAGCC 4080
TGTTGGTGCG GTCATGGAAT TACCTTCAAC CTCAAGCCAG AATGCAGAAT CACTGGCTTT 4140
TTTGGTTGTG CTTACCCATC TCTCCGCATC ACCTTTGGTA AAGGTTCTAA GCTTAGGTGA 4200
GAACATCCCT GCCTGAACAT GAGAAAAAAC AGGGTACTCA TACTCACTTC TAAGTGACGG 4260
CTGCATACTA ACCGCTTCAT ACATCTCGTA GATTTCTCTG GCGATTGAAG GGCTAAATTC 4320
TTCAACGCTA ACTTTGAGAA TTTTGTAAG  CAATGCGGCG TTATAAGCAT TTAATGCATT 4380
GATGCCATTA AATAAAGCAC CAACGCCTGA CTGCCCCATC CCCATCTTGT CTGCGACAGA 4440
TTCCTGGGAT AAGCCAAGTT CATTTTCTT  TTTTTCATAA ATTGCTTTAA GGCGACGTGC 4500
GTCCTCAAGC TGCTCTTGTG TTAATGGTTT CTTTTTTGTG CTCATACGTT AAATCTATCA 4560
CCGCAAGGGA TAAATATCTA ACACCGTGCG TGTTGACTAT TTTACCTCTG GCGGTGATAA 4620
TGGTTGCATG TACTAAGGAG GTTGTATGGA ACAACGCATA ACCCTGAAAG ATTATGCAAT 4680
GCGCTTTGGG CAAACCAAGA CAGCTAAAGA TCCTCTAGCT AGAATTCAGG CTTCTGCCGT 4740
TTTGGATTTA ACCGAAGATG ATTTCGATTT TCTGACGAGT AACAAAGTTT GGATTGCTAC 4800
TGACCGCTCT CGTGCTCGTC GCTGCGTTGA GGCTTGCGTT TATGGTACGC TGGACTTTGT 4860
GGGATACCCT CGCTTTCCTG CTCCTGTTGA GTTATTGCT  GCCGTCATTG CTTATTATGT 4920
TCATCCCGTC AACATTCAAA CGGCCTGTCT CATCATGGAA GGCGCTGAAT TACGGAAAA  4980
CATTATTAAT GGCGTCGAGC GTCCGGTTAA AGCCGCTGAA TTGTTCGCGT TTACCTTGCG 5040
TGTACGCGCA GGAAACACTG ACGTTCTTAC TGACGCAGAA GAAACGTGC  GTCAAAAATT 5100
ACGTGCGGAA GGAGTGATGT AATGTCTAAA GGTAAAAAAC GTTCTGGCGC TCGCCCTGGT 5160
CGTCCGCAGC CGTTGCGAGG TACTAAAGGC AAGCGTAAAG GCGCTCGTCT TTGGTATGTA 5220
GGTGGTCAAC AATTTTAATT GCAGGGGCTT CGGCCCCTTA CTTGAGGATA AATTATGTCT 5280
```

```
AATATTCAAA CTGGCGCCGA GCGTATGCCG CATGACCTTT CCCATCTTGG CTTCCTTGCT  5340
GGTCAGATTG GTCGTCTTAT TACCATTTCA ACTACTCCGG TTATCGCTGG CGACTCCTTC  5400
GAGATGGACG CCGTTGGCGC TCTCCGTCTT TCTCCATTGC GTCGTGGCCT TGCTATTGAC  5460
TCTACTGTAG ACATTTTTAC TTTTTATGTC CCTCATCGTC ACGTTATGG TGAACAGTGG   5520
ATTAAGTTCA TGAAGGATGG TGTTAATGCC ACTCCTCTCC CGACTGTTAA CACTACTGGT  5580
TATATTGACC ATGCCGCTTT TCTTGGCACG ATTAACCCTG ATACCAATAA AATCCCTAAG  5640
CATTTGTTTC AGGGTTATTT GAATATCTAT AACAACTATT TTAAAGCGCC GTGGATGCCT  5700
GACCGTACCG AGGCTAACCC TAATGAGAAT TCTCATGTTT GACAGCTTAT CATCGATAAG  5760
CTTTAATGCG GTAGTTTATC ACAGTTAAAT TGCTAACGCA GTCAGGCACC GTGTATGAAA  5820
TCTAACAATG CGCTCATCGT CATCCTCGGC ACCGTCACCC TGGATGCTGT AGGCATAGGC  5880
TTGGTTATGC CGGTACTGCC GGGCCTCTTG CGGGATATCG TCCATTCCGA CAGCATCGCC  5940
AGTCACTATG GCGTGCTGCT AGCGCTATAT GCGTTGATGC AATTTCTATG CGCACCCGTT  6000
CTCGGAGCAC TGTCCGACCG CTTTGGCCGC CGCCCAGTCC TGCTCGCTTC GCTACTTGGA  6060
GCCACTATCG ACTACGCGAT CATGGCGACC ACACCCGTCC TGTGGATCCG GATCAGCAGG  6120
TGGAAGAGGG ACTGGATTCC AAAGTTCTCA ATGCTGCTTG CTGTTCTTGA ATGGGGGTC   6180
GTTGACGACG ACATGGCTCG ATTGGCGCGA CAAGTTGCTG CGATTCTCAC CAATAAAAAA  6240
CGCCCGGCGG CAACCGAGCG TTCTGAACAA ATCCAGATGG AGTTCTGAGG TCATTACTGG  6300
ATCGCCGGAT CTGAATTGCT ATGTTTAGTG AGTTGTATCT ATTTATTTTT CAATAAATAC  6360
AATTGGTTAT GTGTTTTGGG GGCGATCGTG AGGCAAAGAA AACCCGGCGC TGAGGCCGGA  6420
AGCATAAAGT GTAAAGCCTG GGGTGCCTAA TGAGTGAGCT AACTCACATT AATTGCGTTG  6480
CGCTCACTGC CCGCTTTCCA GTCGGGAAAC CTGTCGTGCC AGCTGCATTA ATGAATCGGC  6540
CAACGCGCGG GGAGAGGCGG TTTGCGTATT GGGCGCCAGG GTGGTTTTTC TTTTCACCAG  6600
TGAGACGGGC AACAGCTGAT TGCCCTTCAC CGCCTGGCCC TGAGAGAGTT GCAGCAAGCG  6660
GTCCACGCTG GTTTGCCCCA GCAGGCGAAA ATCCTGTTTG ATGGTGGTTG ACGGCGGGAT  6720
ATAACATGAG CTGTCTTCGG TATCGTCGTA TCCCACTACC GAGATATCCG CACCAACGCG  6780
CAGCCCGGAC TCGGTAATGG CGCGCATTGC GCCCAGCGCC ATCTGATCGT TGGCAACCAG  6840
CATCGCAGTG GGAACGATGC CCTCATTCAG CATTTGCATG GTTTGTTGAA AACCGGACAT  6900
GGCACTCCAG TCGCCTTCCC GTTCCGCTAT CGGCTGAATT TGATTGCGAG TGAGATATTT  6960
ATGCCAGCCA GCCAGACGCA GACGCGCCGA GACAGAACTT AATGGGCCCG CTAACAGCGC  7020
GATTTGCTGG TGACCCAATG CGACCAGATG CTCCACGCCC AGTCGCGTAC CGTCTTCATG  7080
GGAGAAAATA ATACTGTTGA TGGGTGTCTG GTCAGAGACA TCAAGAAATA ACGCCGGAAC  7140
ATTAGTGCAG GCAGCTTCCA CAGCAATGGC ATCCTGGTCA TCCAGCGGAT AGTTAATGAT  7200
CAGCCCACTG ACGCGTTGCG CGAGAAGATT GTGCACCGCC GCTTTACAGG CTTCGACGCC  7260
GCTTCGTTCT ACCATCGACA CCACCACGCT GGCACCCAGT TGATCGGCGC GAGATTTAAT  7320
CGCCGCGACA ATTTGCGACG GCGCGTGCAG GGCCAGACTG GAGGTGGCAA CGCCAATCAG  7380
CAACGACTGT TTGCCCGCCA GTTGTTGTGC CACGCGGTTG GGAATGTAAT TCAGCTCCGC  7440
CATCGCCGCT TCCACTTTTT CCCGCGTTTT CGCAGAAACG TGGCTGGCCT GGTTCACCAC  7500
GCGGGAAACG GTCTGATAAG AGACACCGGC ATACTCTGCG ACATCGTATA ACGTTACTGG  7560
TTTCACATTC ACCACCCTGA ATTGACTCTC TTCCGGCGCT ATCATGCCAT ACCGCGAAAG  7620
GTTTTGCGCC ATTCGATGGT G                                            7641
```

( 2 ) INFORMATION FOR SEQ ID NO: 6:

( i ) SEQUENCE CHARACTERISTICS:
        ( A ) LENGTH: 3681 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

```
AAATTGTAAA CGTTAATATT TTGTTAAAAT TCGCGTTAAA TTTTTGTTAA ATCAGCTCAT    60
TTTTTAACCA ATAGGCCGAA ATCGGCAAAA TCCCTTATAA ATCAAAAGAA TAGACCGAGA   120
TAGGGTTGAG TGTTGTTCCA GTTTGGAACA AGAGTCCACT ATTAAAGAAC GTGGACTCCA   180
ACGTCAAAGG GCGAAAAACC GTCTATCAGG GCGATGGCCC ACTACGTGAA CCATCACCCT   240
AATCAAGTTT TTTGGGGTCG AGGTGCCGTA AAGCACTAAA TCGGAACCCT AAAGGGAGCC   300
CCCGATTTAG AGCTTGACGG GGAAAGCCGG CGAACGTGGC GAGAAAGGAA GGGAAGAAAG   360
CGAAAGGAGC GGGCGCTAGG GCGCTGGCAA GTGTAGCGGT CACGCTGCGC GTAACCACCA   420
CACCCGCCGC GCTTAATGCG CCGCTACAGG GCGCGTCCCA TTCGCCATTC AGGCTACGCA   480
ACTGTTGGGA AGGGCGATCG GTGCGGGCCT CTTCGCTATT ACGCCAGCTG GCGAAGGGGG   540
GATGTGCTGC AAGGCGATTA AGTTGGGTAA CGCCAGGGTT TTCCCAGTCA CGACGTTGTA   600
AAACGACGGC CAGTGAATTG TAATACGACT CACTATAGGG CGAATTGGAG CTCCACCGCG   660
GTGGCGGCCG CTCTAGTATG GTGCACTCTC AGTACAATCT GCTCTGATGC CGCATAGTTA   720
AGCCAGTATA TACACTCCGC TATCGCTACG TGACTGGGTC ATGGCTGCGC CCCGACACCC   780
GCCAACACCC GCTGACGCGC CCTGACGGGC TTGTCTGCTC CCGGCATCCG CTTACAGACA   840
AGCTGTGACC GTCTCCGGGA GCTGCATGTG TCAGAGGTTT TCACCGTCAT CACCGAAACG   900
CGCGAGGCAG TAAGGTCGGA TGCTTTGTGA GCAATTCGTC CCTTAAGTAA GCAATTGCTG   960
TAAAGTCGTC ACTGTGCGGA TCACCGCTTC CAGTAGCGAC AGAAGCAATT GATTGGTAAA  1020
TTTCGAGAGA AAGATCGCGA GGAAGATCAA TACATAAAGA GTTGAACTTC TTTGTTGTCT  1080
TCGACATGGG TAATCCTCAT GTTTGAATGG CCCTAGAGGA TCCGGCCAAG CTTGCATGCC  1140
TGCAGGTCGA CTCTAGAGGA TCCCCGACGC TCGACGCCAT TAATAATGTT TTCCGTAAAT  1200
TCAGCGCCTT CCATGATGAG ACAGGCCGTT TGAATGTTGA CGGGATGAAC ATAATAAGCA  1260
ATGACGGCAG CAATAAACTC AACAGGAGCA GGAAAGCGAG GGTATCCCAC AAAGTCCAGC  1320
GTACCATAAA CGCAAGCCTC AACGCAGCGA CGAGCACGAG AGCGGTCAGT AGCAATCCAA  1380
ACTTTGTTAC TCGTCAGAAA ATCGAAATCA TCTTCGGTTA AATCCAAAAC GGCAGAAGCC  1440
TGAATGAGAA TTCGACCTCG AGGGGGGGCC CGGTACCCAG CTTTTGTTCC CTTTAGTGAG  1500
GGTTAATTCC GAGCTTGGCG TAATCATGGT CATAGCTGTT TCCTGTGTGA AATTGTTATC  1560
CGCTCACAAT TCCACACAAC ATAGGAGCCG GAAGCATAAA GTGTAAAGCC TGGGGTGCCT  1620
AATGAGTGAG GTAACTCACA TTAATTGCGT TGCGCTCACT GCCCGCTTTC CAGTCGGGAA  1680
ACCTGTCGTG CCAGCTGCAT TAATGAATCG GCCAACGCGC GGGGAGAGGC GGTTTGCGTA  1740
TTGGGCGCTC TTCCGCTTCC TCGCTCACTG ACTCGCTGCG CTCGGTCGTT CGGCTGCGGC  1800
GAGCGGTATC AGCTCACTCA AAGGCGGTAA TACGGTTATC CACAGAATCA GGGGATAACG  1860
CAGGAAAGAA CATGTGAGCA AAAGGCCAGC AAAAGGCCAG GAACCGTAAA AAGGCCGCGT  1920
TGCTGGCGTT TTTCCATAGG CTCGGCCCCC CTGACGAGCA TCACAAAAAT CGACGCTCAA  1980
GTCAGAGGTG GCGAAACCCG ACAGGACTAT AAAGATACCA GGCGTTCCCC CCTGGAAGCT  2040
```

```
CCCTCGTGCG CTCTCCTGTT CCGACCCTGC CGCTTACCGG ATACCTGTCC GCCTTTCTCC 2100
CTTCGGGAAG CGTGGCGCTT TCTCAATGCT CACGCTGTAG GTATCTCAGT TCGGTGTAGG 2160
TCGTTCGCTC CAAGCTGGGC TGTGTGCACG AACCCCCGT  TCAGCCCGAC CGCTGCGCCT 2220
TATCCGGTAA CTATCGTCTT GAGTCCAACC CGGTAAGACA CGACTTATCG CCACTGGCAG 2280
CAGCCACTGG TAACAGGATT AGCAGAGCGA GGTATGTAGG CGGTGCTACA GAGTTCTTGA 2340
AGTGGTGGCC TAACTACGGC TACACTAGAA GGACAGTATT TGGTATCTGC GCTCTGCTGA 2400
AGCCAGTTAC CTTCGGAAAA AGAGTTGGTA GCTCTTGATC CGGCAAACAA ACCACCGCTG 2460
GTAGCGGTGG TTTTTTTGTT TGCAAGCAGC AGATTACGCG CAGAAAAAAA GGATCTCAAG 2520
AAGATCCTTT GATCTTTTCT ACGGGGTCTG ACGCTCAGTG GAACGAAAAC TCACGTTAAG 2580
GGATTTTGGT CATGAGATTA TCAAAAGGA  TCTTCACCTA GATCCTTTTA AATTAAAAAT 2640
GAAGTTTTAA ATCAATCTAA AGTATATATG AGTAAACTTG GTCTGACAGT TACCAATGCT 2700
TAATCAGTGA GGCACCTATC TCAGCGATCT GTCTATTTCG TTCATCCATA GTTGCCTGAC 2760
TGCCCGTCGT GTAGATAACT ACGATACGGG AGGGCTTACC ATCTGGCCCC AGTGCTGCAA 2820
TGATACCGCG AGACCCACGC TCACCGGCTC CAGATTTATC AGCAATAAAC CAGCCAGCCG 2880
GAAGGGCCGA GCGCAGAAGT GGTCCTGCAA CTTTATCCGC CTCCATCCAG TCTATTAATT 2940
GTTGCCGGGA AGCTAGAGTA AGTAGTTCGC CAGTTAATAG TTTGCGCAAC GTTGTTGCCA 3000
TTGCTACAGG CATCGTGGTG TCACGCTCGT CGTTGGTAT  GGCTTCATTC AGCTCCGGTT 3060
CCCAACGATC AAGGCGAGTT ACATGATCCC CCATGTTGTG AAAAAAGCG  GTTAGCTCCT 3120
TCGGTCCTCC GATCGTTGTC AGAAGTAAGT TGGCCGCAGT GTTATCACTC ATGCTTATGG 3180
CAGCACTGCA TAATTCTCTT ACTGTCATGC CATCCGTAAG ATGCTTTTCT GTGACTGGTG 3240
AGTACTCAAC CAAGTCATTC TGAGAATAGT GTATGCGGCG ACCGAGTTGC TCTTGCCCGG 3300
CGTCAATACG GGATAATACC GCGCCACATA GCAGAACTTT AAAAGTGCTC ATCATTGGAA 3360
AACGTTCTTC GGGGCGAAAA CTCTCAAGGA TCTTACCGCT GTTGAGATCC AGTTCGATGT 3420
AACCCACTCG TGCACCCAAC TGATCTTCAG CATCTTTTAC TTTCACCAGC GTTTCTGGGT 3480
GAGCAAAAAC AGGAAGGCAA AATGCCGCAA AAAAGGGAAT AAGGGCGACA CGGAAATGTT 3540
GAATACTCAT ACTCTTCCTT TTTCAATATT ATTGAAGCAT TTATCAGGGT TATTGTCTCA 3600
TGAGCGGATA CATATTTGAA TGTATTTAGA AAAATAAACA AATAGGGGTT CCGCGCACAT 3660
TTCCCCGAAA AGTGCCACCT G                                          3681
```

IMMUNOGENS COMPRISING THE NON-LYTIC MEMBRANE SPANNING DOMAIN OF BACTERIOPHAGES MS2 OR PHIX174

The invention concerns carrier-bound recombinant proteins, a process for their production and their use, in particular as immunogens and vaccines.

The main purpose of the immunological system in humans and animals is to resist and avoid pathological damages which arise as a result of degenerate cells of infectious viruses, bacteria, fungi or protozoa. A special characteristic of the immunological system is that an increasingly stronger resistance occurs after repeated infections with pathogens. The aim of immunization is to build up the power of the immunological system against particular pathogens without causing corresponding diseases.

Antibodies and cellular T and B lymphocytes are responsible for the specific resistance to pathogens. An essential prerequisite for this is the recognition of foreign structures such as e.g. those which occur on a bacterial cell. Depending on the stimulation of the immunological system a temporary or a lifelong immunity to pathogens can be built up in this process after immunization.

It is important for the quality of monoclonal and polyclonal antibodies as well as for the effectiveness of vaccines that the immunological response to the antigen occurs to a sufficient extent. However, viral antigens or recombinant human proteins often show a poor immunological response or none at all if they are used without further modification. For this reason these antigens are often linked to carriers (preferably to proteins) in order to amplify the immunological response. However, the antigens can be changed at or near the antigenic determinants by the binding of the antigens to the carrier. As a result the immunological response can be substantially weakened.

In order to improve the immunological response it is advantageous to incorporate such antigens into the outer membrane of bacteria and to use these complexes as immunogens (J. Immunol. 139 (1987) 1658–1664, Bacterial Vaccines and Local Immunity—Ann. Sclavor 1986, n. 1–2, pp. 19–22, Proceedings of Sclavo International Conference, Siena, Italy, 17–19 November 1986). Attenuated or dead pathogens (bacteria or viruses), treated partial components of pathogens (membrane proteins of bacteria, structural proteins of viruses) or recombinant live vaccines (viruses or bacteria) are also used.

A disadvantage of using live bacteria or viruses as immunogens for the immunization is that an undesired pathogenic spread of the germs cannot be excluded.

However, the antigenic determinant can be altered by killing or fragmenting the bacteria and viruses before their use as an immunogen or vaccine which can substantially reduce the immunological response.

The object of the present invention is therefore to provide immunogens and vaccines which do not have these disadvantages.

This object is achieved via a carrier bound, recombinant protein. This carrier bound, recombinant protein is obtained by expressing a first gene coding for a fusion protein and a second gene, hereinafter referred to as "lysis gene", which codes for one of: (a) a lytically-active, bacteriophage membrane protein, (b) a lytically-active, toxin release gene, or (c) a lytically active, partial sequence of one of these. The fusion protein comprises at least one hydrophobic, non-lytically active protein domain capable of membrane integration and a recombinant protein carrier bound, recombinant protein is then isolated from the culture broth.

The expression of the fusion protein gene and the lysis gene is preferably controlled by two different promoters (FIG. 1). The expression of the lysis gene is preferably delayed with respect to the expression of the fusion protein.

With this type of expression of fusion protein gene and lysis gene one obtains at first the integration of a multitude of fusion proteins into the membrane of the gram-negative bacteria used as the host organism and subsequently lysis of these bacteria takes place. The usually impermeable cell wall complex of the bacteria is made so permeable by this that the cytoplasmic components of the bacteria are released (Eur. J. Biochem. 180 (1989), 393–398). The morphology of the cells, for example the rod-form of E. coli cells, is preserved. A tunnel structure is merely formed in a localized area of the membrane. The tunnel formation is accompanied by a fusion of the inner and outer membrane at the edge of the tunnel. The bacterial coats formed in this way represent the carriers for the recombinant protein and are hereinafter denoted bacterial ghosts (FIG. 2).

The bacterial ghosts consist of a cytoplasmic (inner) membrane, periplasmic space and outer membrane whereby the integrity of the cell wall complex is preserved to a large extent. In the case of bacterial strains which have an additional S-layer coat (paracrystalline protein layer outside the outer membrane) this protein layer is also a component of the bacterial ghosts (Ann. Rev. Microbiol. 37 (1983), 311–339). The bacterial ghosts are therefore carriers of the recombinant proteins (immunogens) and, as a result of their composition (peptidoglycan, lipopolysaccharide), they at the same time constitute the adjuvant for amplifying the immunological response.

All gram-negative bacteria, preferably gram-negative pathogens such as e.g. *Escherichia coli, Bordetella pertussis, Campylobacter jejuni, Corynebacterium diphteriae, Legionella pneumophilia, Listeria monocytogenes, Pseudomonas aeruginosa, Shigella dysenteriae, Vibrio cholerae, Yersinia enterolitica* are suitable as host organisms (Schaechter, M., H. Medoff, D. Schlesinger, Mechanisms of Microbial Disease. Williams and Wilkins, Baltimore (1989)).

The carrier-bound recombinant proteins according to the present invention are surprisingly well suited as immunogens which results in pronounced immunological responses and very high antibody titres.

A particular advantage results from the fact that the recombinant protein is integrated into the membrane of the bacteria directly after the expression and thus the carrier binding is formed. As a consequence it is unnecessary to isolate the recombinant protein as such before production of the immunogen. Moreover, since it is sufficient for the production of bacterial ghosts containing immunogens when from several hundred up to the maximum possible number (ca. 50000) of recombinant antigens are integrated into the membrane of the bacterial ghosts, an over-expression of the recombinant protein is not necessary.

A further advantage of the process according to the present invention is that very many antigenic epitopes are presented in the cell wall complex of the bacterial ghosts. It has turned out that the target sequences for the recombinant proteins prefer certain regions within the bacterial cell wall complex for integration. These regions mainly constitute adhesion sites of the inner and outer membrane and are associated with the cell division of the bacteria. As a result the recombinant protein is not distributed uniformly but rather islet-type accumulations occur within the cell wall complex (cf. FIG. 2d). The clustered arrangement of the recombinant proteins within a relatively small region (cluster) has the advantage that the proliferation of B cells carrying immunoglobulin is stimulated. On the other hand the lipopolysaccharide present in the bacterial ghosts acts as a mitogen and also triggers a signal for the cell division. As a result one achieves an effective stimulation of the B-cell specific production of immunoglobulins.

In addition it has also turned out that the carrier-bound recombinant proteins according to the present invention are integrated into the bacterial membrane in their natural protein structures and thus in an active form.

This is particularly surprising since recombinant proteins are usually obtained in an inactive form as inclusion bodies (cf. EP-A- 0219 874, WO 89/03711) after expression in prokaryotes and can only subsequently be converted into the active form by denaturation and renaturation.

All proteins familiar to one skilled in the art are suitable as recombinant proteins. Human proteins and antigens, in particular viral antigens, are particularly preferably used. Their size is not limited. The molecular weight of the antigens is, however, preferably 2000 to 200000 Daltons.

The recombinant antigen has particularly preferably antigenic structures of human viruses and retroviruses such as e.g. of HIV (human immunodeficiency virus), HBV (hepatitis B virus), and EBV (Epstein Barr Virus)

The hydrophobic non-lytically active protein domains capable of membrane integration are hereinafter denoted target sequences. Complete sequences or partial sequences of membrane proteins which can, however, also be modified by amino acid substitutions are preferred as target sequences. Such a substitution should not, however, alter the structure of the corresponding protein.

Target sequences which are preferably used are those which—in contrast to the signal sequences of other membrane proteins—are not cleaved by proteases which are present in the membrane (e.g. signal peptidase and proteases of the periplasmic space). Target sequences can for example be derived from naturally occurring sequences of the lysis gene of the PhiX174 phage group (for N-terminal targeting) as well as from the naturally occurring sequences of the lysis gene of the MS2 phage group (for C-terminal targeting) by protein engineering.

A hydrophobic alpha-helical protein domain consisting of 14 to 20 amino acids, which can be flanked N- and C-terminally by 2 to 30 arbitrary amino acids each, is preferred as the target sequence. At least one further protein domain can preferably be bound to this protein domain. The binding preferably takes place via flexible linker sequences. Flexible linker sequences are understood as hydrophilic amino acid sequences with 2 to 100 amino acids, preferably with 2 to 30 amino acids and with a disordered secondary structure (turn and random coil sequences).

The additional protein domains which are coupled to the first protein domain can be structured in an analogous manner to the first protein domain. It is, however, preferable that at least one of the additional domains posesses a β-pleated sheet structure and is composed of 10 to 16 amino acids, preferably 11 to 13 amino acids. The construction and secondary structure of such β-pleated sheet structures is preferably similar to amphipathic protein sequences which occur in porins of the outer membranes. For a N-terminal targeting it is preferable to use those target sequences which contain the amino acids 1 to 54 of protein E from the phage PhiX174 (hereinafter denoted E' sequence) and which do not act lytically. For a C-terminal targeting it is preferable to use target sequences which contain the amino acids 21 to 75 of protein L from the phage MS2 (hereinafter denoted L' sequence) and which do not act lytically (for sequences compare EP-A 0 291 021). Sequences which are derived from the above-mentioned sequences of the E and L target sequences by a homologous amino acid substitution which does not cause an alteration in the secondary structure of the protein are also suitable.

Membrane proteins of bacteriophages are preferably understood as membrane proteins from bacteriophages of the Microviridae class, preferably from icosahedral phages, lytic phages and phages containing ssDNA, which can infect Enterobacteriacae. Examples of these are the phages PhiX174, S13, G4, G6, G14, PhiA, PhiB, PhiC, PhiR which can infect E. coli C strains. Alpha 3 which can infect E. coli C and E. coli B strains is also suitable. The phages K9, St-1, PhiK, PhiXtB and U3 which can infect E. coli K12 strains are also suitable (Sinsheimer R. L. (1968) in: Prog. Nucl. Acid Res. Mol. Biol. (Davidson J. N. & Cohn W. W., eds) Vol.8, Academic Press, New York & London, pp. 115–169; Tessman E. S. & Tessmann I. (1978) in: The single-stranded DNA Phages (Denhardt D. T., Dressler D. & Ray D. S., eds.) Cold Spring Harbor Press, Cold Spring Harbor, pp. 9–29; Hayashi M., Aoyama A., Richardson D. L. & Hayashi M. N. (1987) in: The Bacteriophages, pp. 1–71).

Lysis proteins from the mentioned bacteriophages as well as other toxin release genes such as the colicin lysis gene (Microbiol. Sciences 1 (1984) 168–175 and 203–205) are preferably suitable as lytically active membrane proteins.

In a further, preferred embodiment, a binding partner for the recombinant protein is bound to it. This binding partner binds non-covalently. Examples of recombinant protein/ binding partner pairs include, e.g., biotin and (strept)avidin, hapten and antibody, antigen and antibody, concanavalin and antibody, sugar and lectin, hapten and binding protein (e.g., thyroxin binding globulin and thyroxin), and oligopeptide and antibody. Additional substances may, in turn, be bound to the binding partner, either covalently or non-covalently.

Streptavidin, or avidin, and biotin are preferably used as the binding pair. Streptavidin or avidin is especially preferably used as the immobilized recombinant protein and biotinylated antigen is bound to it.

Furthermore, it is preferred that a protein be used as the recombinant protein which recognizes a chemical ligand. Examples for this are β-galactosidase/p-aminophenyl-β-D-thiogalactoside (a structural analogue of lactose), Gene 29 (1984) 27–31. Such substituted products are bound to the bacterial ghosts by the recognition of the active centre of the β-galactosidase without cleavage of the substrate.

The invention also concerns a recombinant DNA which contains a first DNA sequence (DNA target sequence), which codes for at least one hydrophobic non-lytically active protein domain capable of membrane integration, a second DNA sequence (DNA protein sequence) which codes for a recombinant protein, as well as a DNA sequence (DNA lysis gene) which is under separate control from this which codes for a lytically active membrane protein from bacteriophages or a lytically active toxin release gene or for their lytically active parts.

DNA sequences are preferred as DNA target sequences which code for the L' protein or the E' protein. DNA sequences are also suitable which code for amino acid sequences which are derived from these proteins having the same secondary structure. These sequences are preferably connected by DNA sequences which code for hydrophilic protein domains having 2 to 30 amino acids and a disordered secondary structure.

In a preferred embodiment the DNA lysis sequence contains the DNA sequence of the E protein, the DNA sequence of the L protein or the DNA sequence of the EL hybrid protein (for sequences cf. EP-A 0 291 021). Partial sequences thereof which act lytically are also suitable.

The DNA protein sequence is preferably the DNA sequence of a viral antigen (e.g. HIV, HBV, EBV) or of a recombinant human protein.

The invention also concerns a process for the production of a carrier-bound, recombinant protein which is characterized in that a fusion protein which contains at least one hydrophobic non-lytically active protein domain capable of membrane integration as well as a recombinant protein, and a lytically active membrane protein from bacteriophages or a lytically active toxin release gene or lytically active partial sequences thereof are expressed in gram-negative bacteria and the carrier-bound, recombinant protein is isolated from the culture broth. The transformation and expression can be carried out according to processes familiar to one skilled in the art. The transformation is preferably carried out by electroporation or conjugation.

During the fermentation the activity of the lytic protein is preferably at first inhibited or the expression of the lysis gene is repressed and the inhibition or repression is only abolished at a desired time, preferably in the late logarithmic phase.

In a further preferred embodiment the carrier-bound recombinant protein obtained in this way is incubated with a binding partner for the protein which is derivatised, if desired, and the conjugate which is formed is isolated. The above-mentioned partners of the binding pairs are suitable as the binding partner.

In a further preferred embodiment the genes of at least two different recombinant proteins are expressed according to the present invention. In this way immunogens or vaccines can be obtained which have several antigenic structures. In this connection it is particularly preferred to use the antigenic determinants of different viruses or retroviruses (e.g. HIV1, HIV2, HBV and EBV) as the recombinant proteins. For the expression these genes can be arranged in an expression vector either as an open reading frame in the 3' direction after the gene for the target sequence or a special vector can be used for each of the recombinant proteins to be expressed. In this case it is, however, necessary that the vectors are each provided with separate origins of replication and separate resistance genes.

The invention also concerns a process for the production of antibodies which is characterized in that a mammal is immunized with a carrier-bound recombinant protein which is obtainable by expression of a fusion protein in gram-negative bacteria and which contains at least one hydrophobic non-lytically active protein domain capable of membrane integration as well as the recombinant protein, if desired, with a delayed expression of a lytically active membrane protein from bacteriophages or of a lytically active toxin release gene or lytically active partial sequences thereof and the antibodies are obtained from the serum or the spleen according to well-known methods.

In a preferred embodiment B lymphocytes of the immunized animals are fused with a suitable cell line in the presence of transforming agents, the cell line which produces the desired antibodies is cloned and cultured and the monoclonal antibodies are isolated from the cells or the culture supernatant.

It has turned out that the process according to the present invention is particularly suitable for the production of viral immunogens such as e.g. HIV immunogens, HBV immunogens.

In addition, it has surprisingly turned out that the activity and thus the antigenic structures of recombinant antigens, which are usually obtained in an inactive form as refractile bodies (e.g. human proteins such as TPA or G-CSF) when expressed in prokaryotes, are preserved when expressed according to the process according to the present invention. The process according to the present invention therefore proves to be particularly advantageous for the production of immunogenic recombinant human proteins.

The present invention also concerns the use of the carrier-bound recombinant proteins according to the present invention as vaccines and for the stimulation of T lymphocytes.

The vaccines according to the present invention can be produced and used in the usual manner.

The present invention also concerns a process for the production of vaccines using the carrier-bound recombinant proteins according to the present invention. The production of these vaccines can be carried out according to the well-known methods. However, the carrier-bound recombinant protein is preferably first lyophilised and subsequently suspended, if desired, with addition of auxiliary substances.

Furthermore, it is preferred to formulate the vaccine as a multivalent vaccine. For this the carrier-bound recombinant protein according to the present invention can contain several recombinant antigens immobilized on the membrane of the bacterial ghost.

The vaccination with the vaccine according to the present invention can be carried out according to methods which are familiar to those skilled in the art, for example intradermally, intramuscularly, intraperitoneally, intravenously, subcutaneously, orally and intranasally.

For the intramuscular or subcutaneous administration, the vaccine can for example be suspended in physiological saline. For the intranasal or intra-ocular application the vaccine can for example be applied in the form of a spray or an aqueous solution. For local, for example oral, administration it is often necessary to protect the immunogens temporarily against inactivation, for example against saccharolytic enzymes in the cavity of the mouth or against proteolytic enzymes in the stomach. Such a temporary protection can for example be effected by encapsulation of the immunogens. This encapsulation can for example be effected by coating with a protective agent (microencapsulation) or by embedding a multitude of immunogens according to the present invention in a protective carrier (macroencapsulation).

The encapsulation material can be semi-permeable or can become semi-permeable when introduced into the human or animal body. A biologically degradable substance is usually used as the carrier for the encapsulation.

The following examples figures and sequence protocols elucidate the invention further.

FIG. 1 shows diagrams of the plasmids pkSELS, pML1 and pMTV1

FIG. 2a–2d Diagram of a bacterial ghost as a carrier for recombinant proteins a) longitudinal section through a gram-negative bacterium (om: outer membrane; pp: periplasmic space; im: inner (cytoplasmic) membrane, cp: cytoplasm).

b) Formation of a transmembrane lysis tunnel.

c) Cytoplasm flowing out through the lysis tunnel.

d) Bacterial ghost with fusion proteins which are anchored in the cell wall complex via target sequences.

EXAMPLE 1

N-terminal membrane targeting for HIV 1 gp41.

A HIV 1 specific DNA fragment is isolated from plasmid pHF14 as a 1445 bp DNA fragment by partial digestion with HincII/PvuII. The fragment contains the complete sequence of gp41, (345 codons of gp41) linker sequences, the last 45 codons of gp120. It corresponds to the nucleotides 4 to 1448 from SEQ ID NO: 1.

After linearizing plasmid pKSEL5 (SEQ ID NO:6) with AccI and filling up the protruding DNA ends with Klenow polymerase the HIV1 specific DNA fragment is ligated with this linearized plasmid. The plasmid which formed is denoted pHIE1 and contains in frame a fusion of a partial sequence of the E gene (E' target sequence) of PhiX174 with the above-mentioned HIV1 fragment, in which the natural stop codon of the HIV1 env-gene is preserved.

EXAMPLE 2

N- as well as C-terminal membrane targeting of HIV1 gp41.

A 1059 bp HIV1 specific DNA fragment is isolated from the plasmid pHF14 by digestion with HincII. This fragment contains linker sequences at the 5' side followed by 45 codons from gp120 as well as 301 codons from gp41. It corresponds to the nucleotides 4 to 1062 from SEQ ID NO:1. After linearizing plasmid pKSEL5 with AccI and filling up the protruding DNA ends with Klenow polymerase the HIV1 specific DNA fragment is ligated with this vector. The plasmid pHIE3 which formed contains an in frame fusion of a partial sequence of the E gene (E' target sequence) with a partial sequence of HIV and a partial sequence of the L gene (L' target sequence ).

EXAMPLE 3

C-terminal membrane targeting of HIV1 gp41.

A 1061 bp DNA fragment is isolated from plasmid pHF14 with SalI and HincII. This fragment contains linker sequences on the 5' side followed by 45 codons of gp120 as well as 301 codons of gp41. It corresponds to the nucleotides 2 to 1062 from SEQ ID NO: 1. After removing the E' sequence from the plasmid pKSEL5 by digestion with XhoI/AccI the protruding DNA ends of the vector and of the isolated HIV1 fragment are filled up with the aid of Klenow polymerase and, ligated. The plasmid pHIE5 which formed contains an in frame fusion of the first 5 codons of the lacZ gene, polylinker codons, gp120/gp41 codons and polylinker codons followed by the L' target sequence.

EXAMPLE 4

C-terminal membrane targeting of streptavidin.

The 498 bp XbaI fragment (FXaStrpA, nucleotide 2 to 499 of SEQ ID NO:2) from pFN6 filled up with Klenow polymerase is ligated into the filled up cleavage sites of the plasmid pKSEL5 from which the E' gene fragment was deleted by cleavage with HincII/XhoI. The plasmid obtained is denoted pAV5. This gives rise in the plasmid pAV5 to an in frame fusion of the first5 codons of the LacZ gene, 26 amino acid codons from the remaining polylinker sequence as well as of the amino acid sequences of the FXaStrpA part followed by the L' target sequence.

EXAMPLE 5

N-terminal membrane targeting of streptavidin.

The streptavidin gene extended on the 5' side by a factor Xa protease cleavage site is isolated as a 511 bp fragment from plasmid pFN6 after digestion with BamHI. It contains nucleotides 14 to 524 from SEQ ID NO:2. After filling up the ends with Klenow polymerase this DNA fragment is integrated into the filled up XbaI cleavage site of vector pKSEL5 between the E' and L' target sequences. An in frame gene fusion thereby results in plasmid pAV1 consisting of the E' target sequence and the FXaStrpA sequence. The stop codons occurring on the 3' side of streptavidin remain intact by the cloning which was carried out.

EXAMPLE 6

N- and C-terminal membrane targeting of streptavidin.

The stop codons 5'-TAATAA-3' which are located behind the streptavidin gene in plasmid pAV1 are removed by deletion of a 33 bp long DNA fragment which is produced by partial digestion with HincII and subsequent digestion with XbaI. The streptavidin-specific DNA sequence contains nucleotides 14 to 499 from SEQ ID NO:2. After filling up the plasmid ends with Klenow polymerase and religating, the L' target sequence included on the vector is fused in frame to the E' target sequence and the FXaStrpA sequence (plasmid pAV3). The corresponding gene product is thus provided with an N- as well as a C-terminal target sequence.

EXAMPLE 7

N-terminal membrane targeting of β-galactosidase.

A 3124 bp DNA fragment (SEQ ID NO:3) is isolated from the plasmid pMC1403 (J. Bacteriol. 143 (1980) 971–980) with the aid of PstI and DraI and ligated in the correct orientation into the PstI and NruI restriction sites of the plasmid pKSEL5. The plasmid pLZl which formed contains the first 54 codons of the E' target sequence, 13 linker codons and 1015 codons of the LacZ gene. The PstI/DraI fragment used for plasmid pLZ1 extends in the sequence protocol SEQ ID NO:3 from nucleotide 26 to 3149 inclusive and comprises 3124 bp.

EXAMPLE 8

N- and C-terminal membrane targeting of β-galactosidase.

The 3010 bp LacZ DNA fragment (PstI-EcoRI; nucleotides 26 to 3035 from SEQ ID NO: 3) is isolated from plasmid pMC1403 and is integrated in the correct orientation into the PstI/HindIII restriction site of pKSEL5 after filling up the EcoRI and HindIII ends. In the plasmid pLZ3 thus obtained this results in an in frame fusion of the E' target sequence with the LacZ gene and the L' target sequence.

EXAMPLE 9

C-terminal membrane targeting of β-galactosidase.

Plasmid pLZ3 is digested with EcoRI and partially digested with AccI. The E' target sequence is thereby removed. The fragment contains the nucleotides 29–3035 from SEQ ID NO:3 and is 3007 bp long (after filling up the EcoRI cleavage site). After filling up the protruding DNA ends of the vector and religating, the vector pLZ5 results in which a lacZ-L' fusion gene is present and the gene product of which has a C-terminal membrane target sequence.

EXAMPLE 10

Production of the carrier-bound recombinant proteins via the plasmids pMTVl (SEQ ID NO:4), pkSEL and pMLl (SEQ ID NO:5).

A lysis cassette is present on the plasmids pMTVl and pMLl consisting of the lambda cI857 repressor gene, the lambda promotor/operator system pR on the right side as well as the PhiXl74 lysis gene E. The integration of the foreign gene can be carried out in the multiple cloning site mcs 2 for pMTV1 or pkSEL5 (FIG. 1). This is carried out in an analogous manner to that described in Examples 1–9.

EXAMPLE 11

Fermentation and lysis

The plasmid is integrated into *E. coli* K12 (DSM 2093) and the culture is grown in a shaking flask up to OD 0.8–1.2 at 600 nm whereby the expression of the lysis gene E is repressed by cI857 repressor molecules (Eur. J. Biochem. 180 (1989) 393 to 398). The expression of gene E by thermal inactivation of cI857 repressor molecules is carried out by increasing the temperature to 42° C. during the exponential growth phase of the bacteria. The lysis of *E. coli* caused by protein E starts between 10 and 30 min after increasing the temperature depending on the culture medium of the bacteria (total medium or minimum medium, under aeration in a shaking water bath). After a further 10 to 30 min the lysis is completed.

EXAMPLE 12

Modified protein E-lysis

The culture is as in Example 11 in which, however, the culture medium is made up to 0.2 mol/l magnesium sulphate by adding magnesium sulphate solution 30 min prior to increasing the temperature from 28° C. to 42° C. This prevents the lysis of the bacteria despite the expression of gene E.

The cells are harvested by centrifugation 30 min after increasing the temperature. An instantaneous lysis of the cells is effected by resuspension of the cell pellet in low molar buffer (PBS, 1 mmol/l phosphate buffer, 1 to 10 mmol/l Tris-HCl pH 6–8) or water. The cell coats which are obtained in this process are denoted bacterial ghosts. Under these conditions, which correspond to a combination of protein E lysis and osmotic shock, a larger lysis structure is obtained in the bacteria. The morphology of the bacterial ghosts is also preserved to a large degree under these conditions.

The bacterial ghosts are washed 2× with PBS or 0.9% NaCl for purification (resuspending and centrifuging) and lyophilized.

EXAMPLE 13

Immunization

For the immunization, $10^9$ germs (corresponding to 1 mg dry weight of bacterial ghosts) per mouse are administered 4× intraperitoneally in 0.9% NaCl at monthly intervals. 8 days after the last immunization serum is obtained and the antibodies are isolated.

EXAMPLE 14

Binding of biotinylated HBc antigen

Bacterial ghosts produced according to example 4, into which streptavidin is integrated via target sequences, are lyophilized. 10 ml of a solution of 20 Ig/ml of a conjugate of hepatitis B core antigen and biotin (produced by reaction of HBcAg with N-hydroxysuccinimide-activated biotin) in 40 mmol/l phosphate buffer, pH 7.4 is added to 1 mg of this lyophilisate, incubated for 30 min and subsequently washed several times with 40 mmol/l phosphate buffer, pH 7.4. In this way a carrier-bound HBcAg immunogen is obtained which can be used for immunization and isolation of antibodies.

---

We claim:

1. Immunogen comprising a non-lytic fusion protein bound to a portion of a gram negative bacterial cell membrane, wherein said fusion protein comprises:
   (i) one hydrophobic, non-lytically active protein domain capable of integration into a gram negative bacterial cell membrane wherein said hydrophobic, non-lytically active protein domain is selected from the group consisting of: (a) amino acids 1 to 54 of protein E of phage Phix174, and (b) amino acids 21 to 75 of protein L of phage MS2, and
   (ii) a protein foreign to a gram negative bacteria in which said fusion protein is expressed.

2. The immunogen of claim 1, wherein said at least one hydrophobic, non-lytically active protein domain and said foreign protein are linked by a hydrophilic amino acid sequence of from 2 to 100 amino acids.

3. The immunogen of claim 1, wherein said hydrophic, non-lytically active protein domain and said protein foreign to said gram negative bacteria are linked to each other via from 10 to 16 amino acids which have a β pleated secondary structure.

4. The immunogen bacteria of claim 1, wherein said protein foreign to said gram negative bacteria is antigenic.

5. The immunogen of claim 1, further comprising a non-covalently bound binding partner bound to said foreign protein.

6. The immunogen of claim 1, further comprising an additional substance bound to said binding partner.

7. The immunogen of claim 5, wherein said protein foreign to said gram negative bacteria comprises the protein portion of streptavidin or avidin.

8. The immunogen of claim 5, wherein said covalently bound binding partner is a biotinylated antigen.

* * * * *